United States Patent [19]

Boyce

[11] Patent Number: 4,828,400

[45] Date of Patent: May 9, 1989

[54] STRESS ANALYZER WITH AUTOMATIC OVERLOAD RESPONSE

[75] Inventor: Bradley R. Boyce, Beaver Dam, Wis.

[73] Assignee: Deere & Company, Moline, Ill.

[21] Appl. No.: 204,052

[22] Filed: Jun. 8, 1988

[51] Int. Cl.⁴ .............................................. G01N 3/00
[52] U.S. Cl. ........................................ 374/46; 374/47; 374/124
[58] Field of Search .................... 73/808, 811, 1 B; 374/46–48, 141, 142, 124; 364/508; 250/359.1, 360.1

[56] References Cited

U.S. PATENT DOCUMENTS

4,541,059 9/1985 Toshihiko .............................. 73/808

Primary Examiner—Stewart J. Levy
Assistant Examiner—Robert R. Raevis

[57] ABSTRACT

An object stress analyzing system includes a scanning head with a detector, a variable gain amplifier and a control unit which controls the scanning head and which acquires stress-related data from the amplifiers. The control unit responds to detector overload conditions by automatically adjusting the gain of the amplifier, rescanning a portion of the object and rescaling data acquired prior to occurrence of the overload condition.

7 Claims, 4 Drawing Sheets

STRESS ANALYZER WITH AUTOMATIC OVERLOAD RESPONSE

BACKGROUND OF THE INVENTION

The present invention relates to a system for measuring stress in an object.

A portion of the disclosure of this patent document contains material to which is subject to a claim of copyright protection. The copyright owner has no objection to the facsimile reproduction by anyone of the patent document or the patent disclosure, as it appears in the Patent and Trademark Office patent file or records, but otherwise reserves all other rights whatsoever.

Various non-destructive techniques have been proposed to measure and analyze stresses in a physical object. For example, U.S. Pat. No. 4,378,701 discloses a technique whereby stress is analyzed by detecting thermal radiation produced by a part subject to stress. This technique is utilized in a computer controlled stress analyzing system (SPATE 8000) marketed by Ometron, Inc.. This known system detects the minute temperature changes which arise when an object is cyclically loaded. These temperature changes are correlated with a reference signal which represents the applied load. However, this known system may produce inaccurate results due to overload conditions caused by intermittent thermal disturbances or caused by a strong source of thermal radiation source moving into the field of view of the scanning infra-red detector.

If an operator is not present during occurrence of the overload condition, then the known system will retain faulty data caused by the overload. If an operator is present and recognizes an overload situation, the operator can manually adjust the sensitivity to eliminate the overload condition. However, the system will then have acquired two sets of data obtained under different conditions, thus preventing the uniform displaying of such data.

SUMMARY OF THE INVENTION

An object of the present invention is to provide a scanning stress analyzing system which is not adversely effected by object or non-object produced temporary or intermittent thermal disturbances.

Another object of the present invention is to provide such a system wherein detector sensitivity is automatically adjusted in response to overloads Another object of the present invention is to provide such a system wherein data collected before and after such a thermal disturbance is automatically recalibrated.

A further object is to provide such a system wherein an object may be automatically partially rescanned in response to an overload condition.

These and other objects are achieved by the present invention which responds to overload conditions by automatically adjusting the gain of the amplifier, rescanning a portion of the object and rescaling data acquired prior to occurrence of the overload condition so that a consistent set of data for the entire scan is acquired.

DETAILED DESCRIPTION

Figure 1:
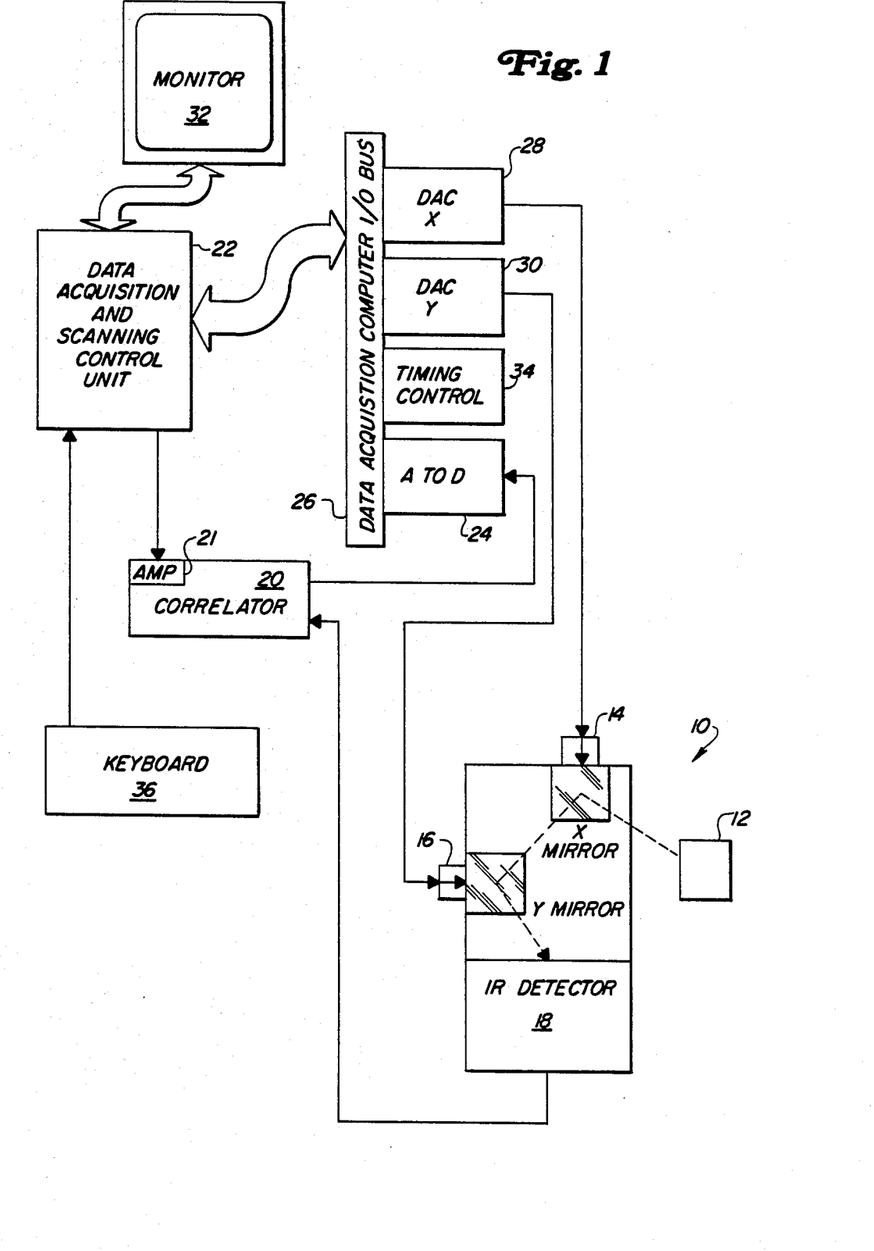
FIG. 1 is a simplified schematic diagram of a stress analyzing system in which the present invention operates.

An optical stress analyzing system, shown schematically in FIG. 1, includes a known scanning head unit 10 which operates to optically scan stress-produced thermal radiation emitted by the object to be analyzed 12. Such a scanning head is described in detail in U.S. Pat. No. 4,378,701 issued to Mountain et al. in 1983. The scanning head includes x and y mirror drive motors 14, 16 and an infra-red detector 18. A correlator or lock-in amplifier 20 receives the signal from detector 18. The correlator is preferably an off-the-shelf item, such as the EG & G Models 5206 or 5208 lock-in amplifier. The correlator 20 includes a variable gain amplifier 21, the gain of which may be controlled by control signals coupled thereto. The correlator 20 provides a voltage which represents the amplitude of the detector signal.

The amplified detector signal is supplied to a data acquisition and scanning control unit 22 via analog-to-digital converter 24 and I/O Bus 26. The control unit 22 causes the head 10 to scan the object by moving drive motors 14 and 16 in a step-by-step manner via x and y digital-to-analog converters (DAC) 28 and 30, and provides information for display on a monitor 32. At each position during a scan, the correlator 20 receives data from the detector 18 and communicates this data to the control unit 22.

A timing control circuit 34 includes a programmable timer which operates to coordinate operation of data acquisition via A-to-D converter 24 and mirror movement via DACs 28 and 30. The control unit 22 includes a digital computer programmed to perform data acquisition loop and scanning control functions. Such control units are included in the SPATE 8000 systems available from Ometron Inc.. Operator control is provided via a keyboard 36.

Figure 2A:
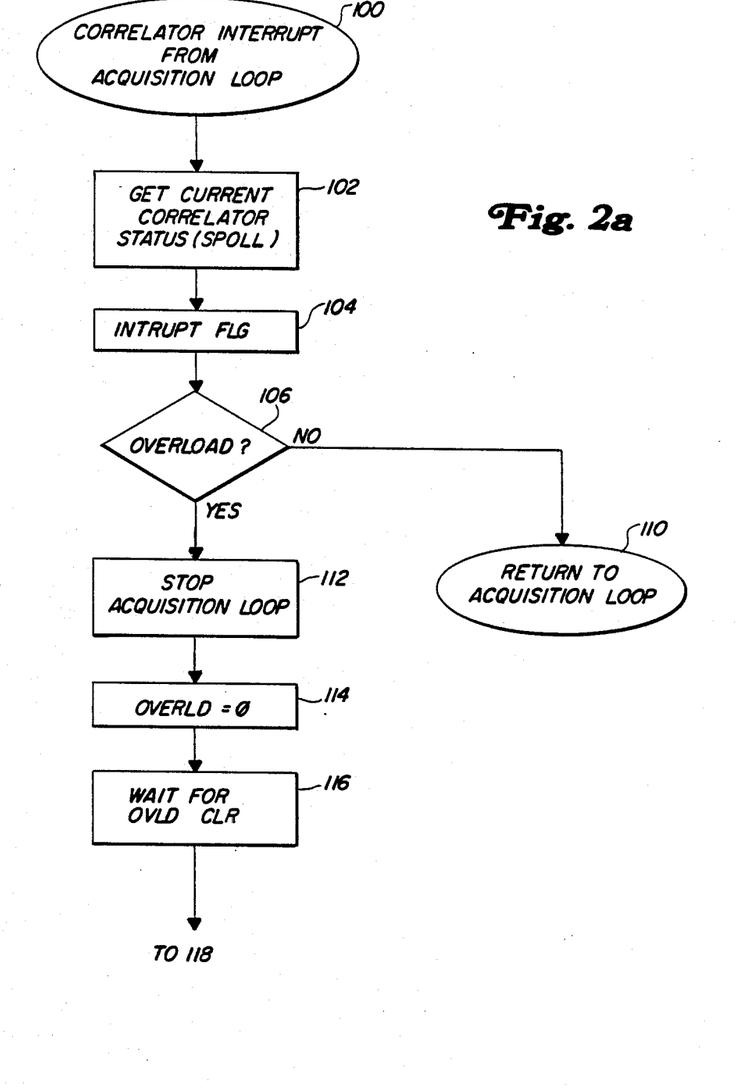
FIGS. 2a–2c are simplified flow charts of the overload-responsive algorithm of the present invention.

According to the present invention, the control unit is provided with an additional overload condition responsive algorithm which will now be described with reference to FIG. 2a. The algorithm is entered from the main or data acquisition loop at step 100 in response to a system interrupt. Then, in steps 102 and 104, the status of the correlator is examined and an interrupt flag is set equal to 1.

If, in the meantime, the overload condition has disappeared, then step 106 causes the algorithm to proceed to step 110 which causes a return to the data acquisition loop without disruption. If the overload condition is due to too large a signal magnitude from detector 18, then step 106 directs the algorithm to step 112 which stops operation of the data acquisition loop, to step 114 which sets a counter value, OVERLD, equal to zero, and then to step 116 which causes the algorithm to pause for approximately 1 second.

Then, the correlator status is examined again in step 118. If the overload condition has disappeared at this step, then step 120 directs the algorithm to step 122 which causes the mirror drives 14, 16 to back up a few steps. Then, step 124 returns to and restarts the head scanning and data acquisition loop so that new data will be acquired to replace the data which included the overload condition.

Figure 2B:
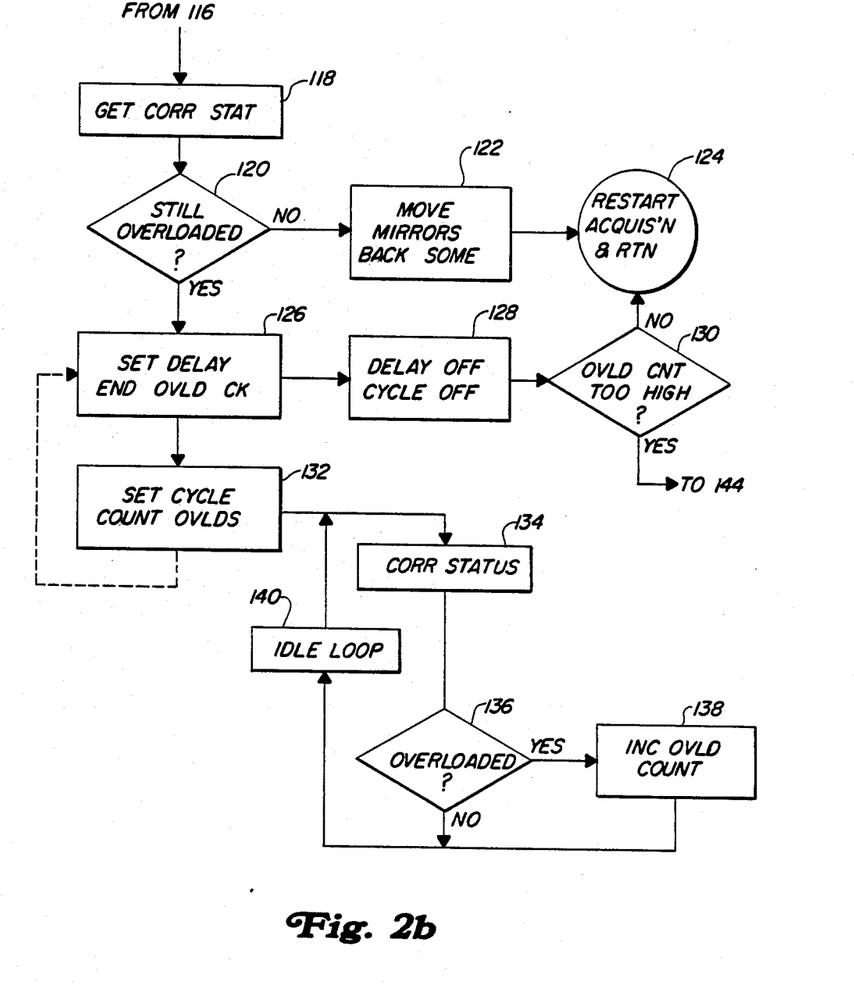

If, in step 120, the overload condition still exists, then the algorithm proceeds to steps 126–140. This group of steps operates to count up the number of times the overload condition is present during a certain time period, such as 5 to 10 seconds. During this period, the overload condition is examined periodically, such as every 0.1 seconds, and an OVERLD counter value is incremented for each overload occurrence. After the number of overload conditions have been counted during this time period, step 126 routes the algorithm to step 128 which turns off the delay and cycle associated with this overload counting loop. If less than a certain number of overloads have occurred (about 30, for example), then step 130 directs the algorithm back to the data acquisition loop via step 124.

If more than about 30 overloads have occurred, then the algorithm proceeds to step 144 which determines whether the system is displaying on monitor 32 information relating to the data being acquired. If not, the algorithm proceeds to steps 146–150 which operate to automatically adjust the sensitivity of the correlator 20 by one step, to correspondingly adjust the scaling factor relating to the data collected, to cause the mirror drives 14 and 16 to reposition the mirrors in the scanning head to re-execute a small part of the scan just completed so that the data including the overloads can be replaced.

Finally, step 152 returns to and restarts the data acquisition loop.

Figure 2C:
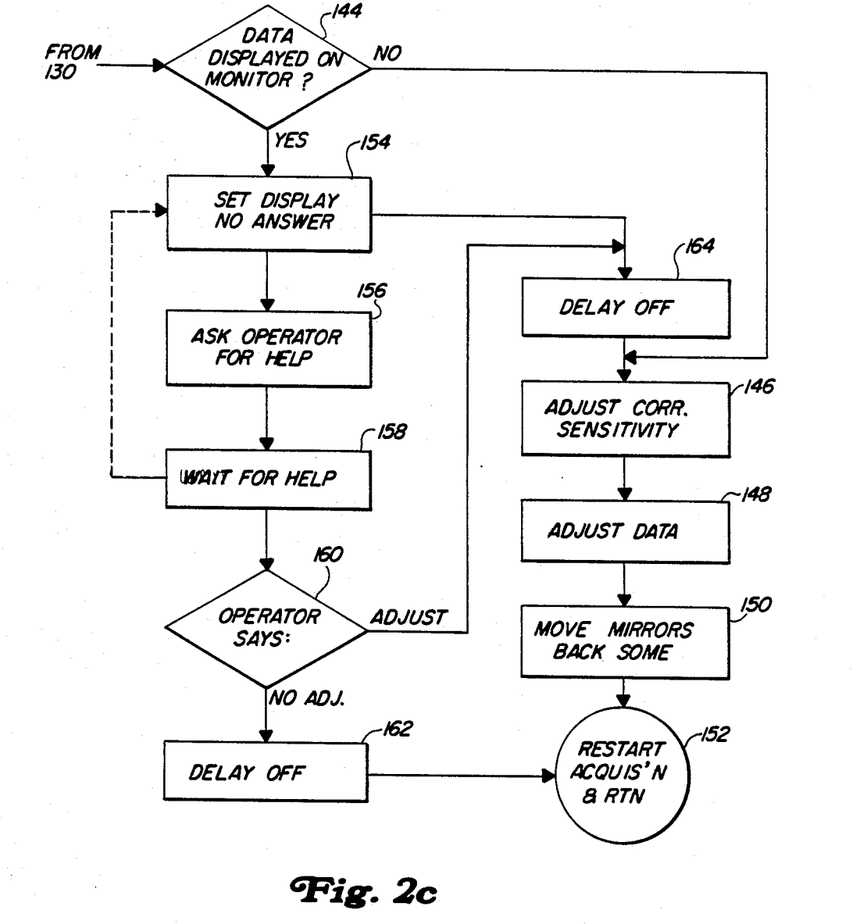

Returning to step 144, if data is being displayed on a monitor, then the algorithm proceeds to steps 154–158 which operate to cause a delay of 2 minutes (for example) while the computer waits for a human operator to enter a command via the keyboard 34. If no operator command is entered, then when the 2 minute delay period expires, the algorithm will proceed to step 164 which ends the delay period and then to previously described steps 146–152. If an operator command is entered, then step 160 directs the algorithm to previously described steps 164 and 146–152 if the operator commands that the correlator sensitivity be adjusted. If the operator commands no adjustment, then step 160 directs the algorithm to step 162 which turns off the delay timer and then back to the data acquisition loop via step 152.

The following is a program listing of a computer program in the Basic language which operates as just described in connection with the flow charts of FIGS. 2a-2c.

```
873   !
874
!************************************************
***
875   !           S C A N    U T I L I T I E S
876
!************************************************
***
877   !
878 Inc_pos: !
879    SELECT Scan_mode
880    CASE 0                                    ! Point
881      Point=Point+1
882      IF Point>Num_pts THEN Point=1
883      Pos_x=Scan_list(Point+1,1)
884      Pos_y=Scan_list(Point+1,2)
885    CASE 1                                    ! Line
886    CASE 2                                    ! Area
887      CALL Pos_fwd(Scan_list(*),List_count,I,Pos_x,Pos_y,Posx_1,Posy_1)
888    END SELECT
889    RETURN
890    !
891 Dec_pos:   !
892    SELECT Scan_mode
893    CASE 0                                    ! Point
894      Point=Point-1
895      IF Point<1 THEN Point=Num_pts
896      Pos_x=Scan_list(Point+1,1)
897      Pos_y=Scan_list(Point+1,2)
```

```
898      CASE 1                                          ! Line
899      CASE 2                                          ! Area
900        CALL Pos_bwd(Scan_list(*),List_count,I,Pos_x,Pos_y,Posx_1,Posy_1)
901      END SELECT
902      RETURN
903        !
904        !
905 Back_some:     !
906      FOR J=1 TO Back_much
907        GOSUB Dec_pos
908      NEXT J
909      RETURN
910        !
911        !
912 Corr_overld:   !
913 Corr_stat:     !
914      Cor_stat=SPOLL(Cor_adrs)
915      Corr_intr_flg=1
916      GOTO Ck_cor_ovld                                ! This is to provide a quick
917                                                      ! unstopped check of overload
918        !
919        !
920 Ck_ref_low:    !
921      PRINT "Checking if ref is low"
922      PRINT Cor_stat
923      IF BIT(Cor_stat,3) THEN
924        GOSUB Stop_scan                               ! Make sure scanning is stop'd
925        PRINT "REFERENCE signal is low. Please remedy."
926        Bit3=1
927        Req=64+4                                      ! Request main cpu help
928        REQUEST Mnib;Req                              ! Signal ref low
929      ELSE
930        IF Bit3 THEN PRINT "Reference is back on"     ! CLEAR DISP MESSAGE
931        Corr_intr_flg=0                               ! Reset intrupt flg
932        CONTROL Mnib,1;0                              ! Clear SRQ
```

```
933        GOTO Intr_ret                              ! and continue scanning
934    END IF
935        !
936        !
937        !
938 Ck_cor_ovld:    !
939    IF NOT (BIT(Cor_stat,4)) THEN                  ! CHECK OVERLOAD
940       GOTO Commands
941    END IF
942    Overld=0                                       ! OVERLOAD
943    WAIT Clr_ovld_wait                             ! Overload delay
944    Cor_stat=SPOLL(Cor_adrs)
945    IF NOT (BIT(Cor_stat,4)) THEN
946       GOSUB Back_some
947       GOTO Intr_ret
948    END IF
949    ON DELAY Ck_ovlds_time,8 GOTO End_ovrld_ck     ! Overload check time
950    ON CYCLE 10,7 GOSUB Overld_ck
951    GOTO Idle
952        !
953 Overld_ck: !
954    Cor_stat=SPOLL(Cor_adrs)
955    IF BIT(Cor_stat,4) THEN
956       Overld=Overld+1                             ! Overload not gone after dely
957    END IF                                         ! count overload in check time
958    RETURN
959        !
960 End_ovrld_ck:   !
961    OFF DELAY
962    OFF CYCLE
963    IF Overld<=Ovld_ok_cnt THEN                    ! Allowed overloads
964       GOTO Intr_ret
965    ELSE
966       PRINT "Experiencing continual overloading.  Can you help me?"
967        !
968       IF Main_mon THEN
969          Req=64+2
970          REQUEST Mnib;Req                         ! Signal adjust
971          ON DELAY 120,8 GOTO Adj_down
```

```
972      ELSE
973         GOTO Adj_down
974      END IF
975      A=TIMEDATE
976      ON CYCLE 10,7 GOSUB Sec_to_down
977      GOTO Idle
978         !
979 Sec_to_down:       !
980      PRINT PROUND(120-(TIMEDATE-A),0);" seconds until automatic senesitivity adjustment."
981      SOUND 1,600,15,.05
982      RETURN
983         !
984 Adj_down:          !
985      OFF DELAY
986      OFF CYCLE
987      GOSUB Read_new_sens                    !Get current sensitivity
988      Correl_sens=Correl_sens_new
989      Ans1=Ans1-1                            !Lower the sensitivity
990      CALL Cor_w(Cpu_confg,Cor_adrs,"S",Correl_cntld,Ans1)   !Set new sensitivity
991      GOSUB Read_new_sens
992      MAT Stress_data= Stress_data*(Correl_sens/Correl_sens_new)
993      MAT Cal_factors= Cal_factors*(Correl_sens_new/Correl_sens)
994      Correl_sens=Correl_sens_new
995      MAT Data= (0)                          ! Zero out current data buffers
996      MAT Datb= (0)
997      WAIT Clr_ovld_wait                     ! Overload delay
998      GOTO Over_ld_done
999      END IF
1000        !
1001 Read_new_sens:    !
1002 CALL Cor_r(Cpu_confg,Cor_adrs,"S",Correl_cntld,Ans1)  !READ new sensitivity
1003 Ans2=Ans1-(INT(Ans1/3)*3)+1
1004 IF Ans2=1 THEN Ans2=5
1005 IF Ans2=3 THEN Ans2=1
1006 Correl_sens_new=(10^(-1*(INT(Ans1/3))))*Ans2*1000
1007 RETURN
```

```
1008     !
1009 No_adj:    !
1010    OFF DELAY
1011    OFF CYCLE
1012    PRINT "No adjustment made"
1013 Over_ld_done:!
1014    !
1015    !
1016 Intr_ret:    !                              ! Continue scanning
1017    GOSUB Back_some
1018    Cor_intr_flg=0
1019    Main_mon=1
1020    GOSUB Correl_key                         ! Reenable correl
interupts
1021    GOSUB Data_acq_prep
1022    ON TIMEOUT Mnib,.15 GOSUB Scan_cmds
1023    SELECT Scan_mode
1024    CASE 0                                   ! Pt mode
1025       GOTO Re_enter_pt
1026    CASE 1                                   ! Line mode
1027       GOTO Re_enter_ln
1028    CASE 2                                   ! Area mode
1029       GOTO Re_enter_ar
1030    END SELECT
1031    !
```

While the invention has been described in conjunction with a specific, embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. In an apparatus for analyzing stress in an object, including a detector for detecting stress-related radiation emitted by the object and for generating signals indicative thereof, a scanner for scanning the detector across the object in response to scan control signals applied thereto, a variable gain amplifier for amplifying the signals generated by the detector, and a control unit for acquiring the amplified signals form the amplifier and generating the scan control signals, characterized by the control unit comprising:

means for detecting an overload condition; and
means for automatically causing the scanner to rescan a portion of the object if the overload condition disappears within a certain time period.

2. The control unit of claim 1, further comprising:
means for stopping acquisition of signals from the detector in response to detection of the overload condition and before the object is rescanned; and
means for resuming acquisition of signals from the detector as the object is rescanned.

3. The control unit of claim 1, further comprising:
means for automatically adjusting the gain of the variable gain amplifier in response to occurrence of the overload condition.

4. The apparatus of claim 3, further comprising:
a monitor for displaying data acquired by the control unit, the control unit comprising means for delaying automatic gain adjustment for a certain time period if data acquired by the control unit is being displayed on the monitor.

5. The control unit of claim 1, further comprising:
means for automatically adjusting a scaling factor relating to data acquired before and after ocurrence of the overload condition.

6. The control unit of claim 1, wherein the overload detecting means comprises:

means for counting overload occurrences during a certain time period.

7. In an apparatus for analyzing stress in an object, including a detector for detecting stress-related radiation emitted by the object, a scanner for scanning the detector across the object in response to scan control signals applied thereto, a variable gain amplifier for amplifying signals from the detector, and a control unit for acquiring amplified detector signals and generating scan control signals, characterized by the control unit comprising:

means for detecting an overload condition;

means for stopping acquisition of signals from the detector;

means for automatically adjusting the gain of the variable gain amplifier;

means for automatically adjusting a scaling factor relating to detector signals acquired by the control unit before and after the overload condition; and means for automatically causing the scanner to rescan a previously scanned portion of the object and then to continue scanning unscanned portions of the object.

* * * * *